United States Patent [19]

Greenfield

[11] Patent Number: 5,035,614
[45] Date of Patent: Jul. 30, 1991

[54] INTRUDING AND TORQUING AUXILIARY

[75] Inventor: Raphael L. Greenfield, Boca Raton, Fla.

[73] Assignee: TP Orthodontics, Inc., Westville, Ind.

[21] Appl. No.: 466,516

[22] Filed: Jan. 17, 1990

[51] Int. Cl.$^5$ .............................................. A61C 3/00
[52] U.S. Cl. ..................................... 433/21; 433/18; 433/20
[58] Field of Search ....................... 433/10, 11, 16, 17, 433/18, 21, 24, 20

[56] References Cited

U.S. PATENT DOCUMENTS

| | | | |
|---|---|---|---|
| 3,237,305 | 3/1966 | Hegedus | 433/21 |
| 3,508,332 | 4/1970 | Armstrong | 433/21 |
| 3,793,730 | 2/1974 | Begg et al. | 433/21 |
| 3,975,823 | 8/1976 | Sosnay | 433/21 |
| 4,595,361 | 6/1986 | Blechman et al. | 433/18 |
| 4,676,747 | 6/1987 | Kesling | 433/18 |
| 4,842,514 | 6/1989 | Kesling | 433/21 |

Primary Examiner—Gene Mancene
Assistant Examiner—Michael Lynch
Attorney, Agent, or Firm—Lloyd L. Zickert

[57] ABSTRACT

An orthodontic auxiliary appliance for intruding and torquing upper anterior teeth, which includes the use of an auxiliary archwire gingival to the main archwire and slidably retained by buccal tubes, together with a unique connecting auxiliary extending between the main archwire and the auxiliary archwire or between the brackets on the anterior teeth and the auxiliary archwire, which connecting auxiliary includes an anchoring portion, an intermediate coiled portion, and a hook.

10 Claims, 2 Drawing Sheets

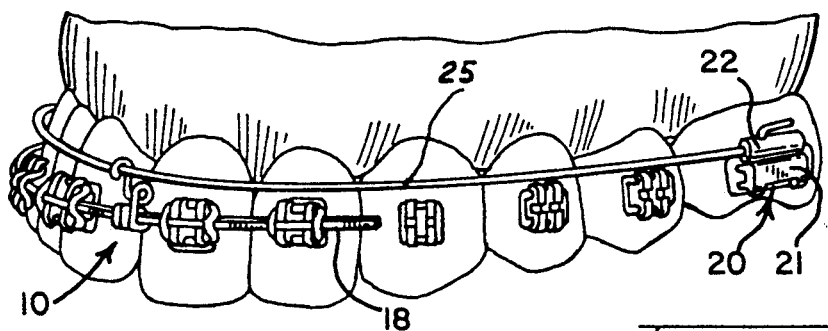
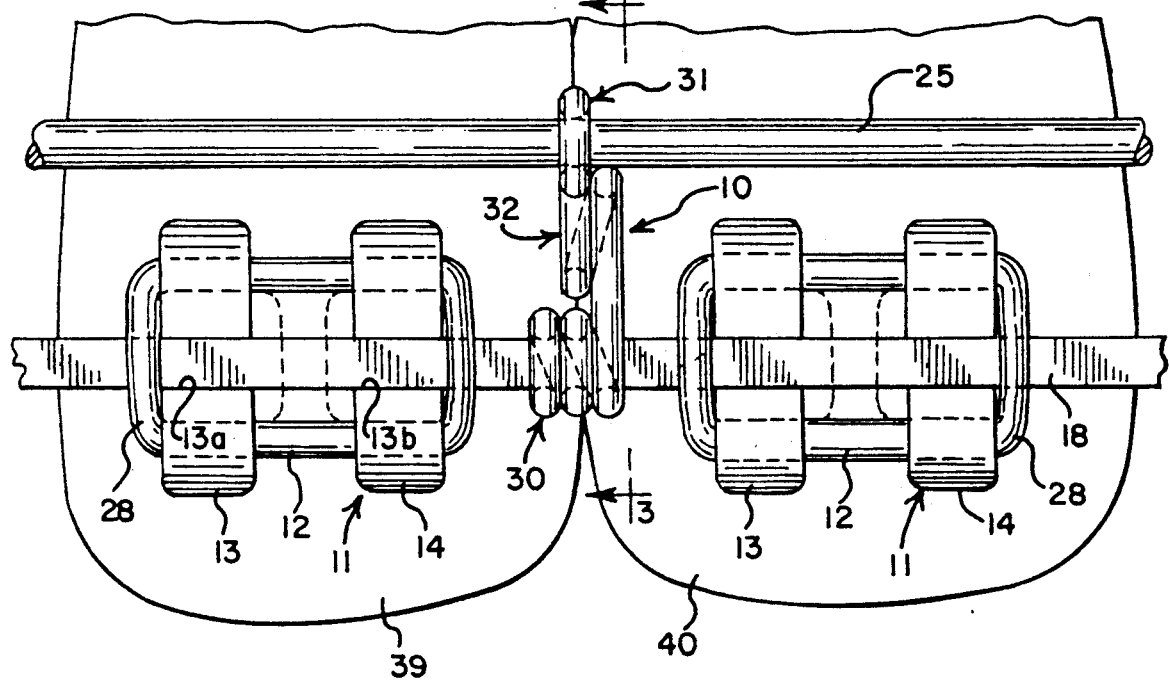
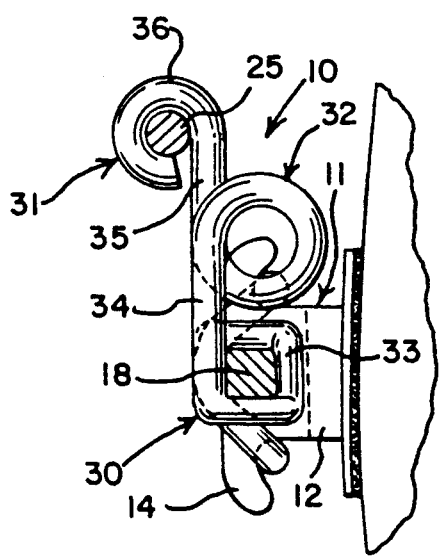

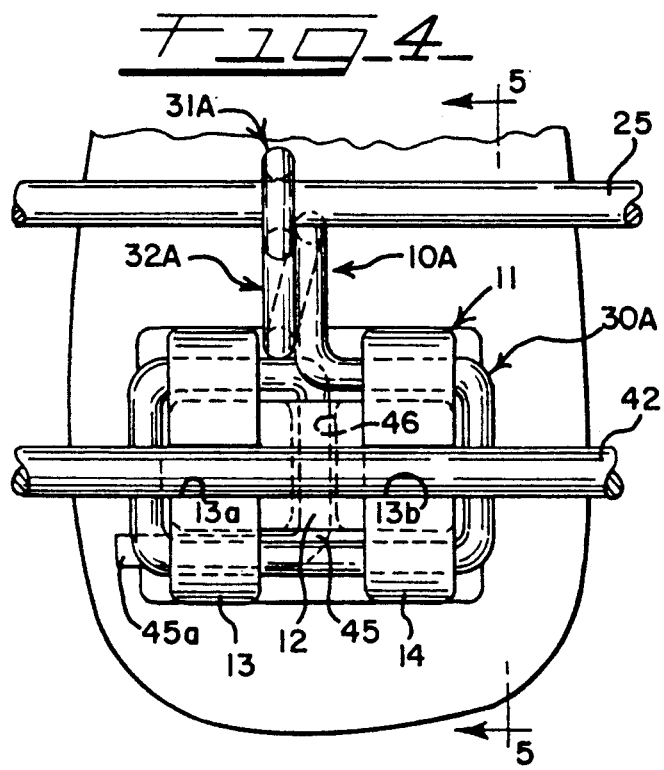
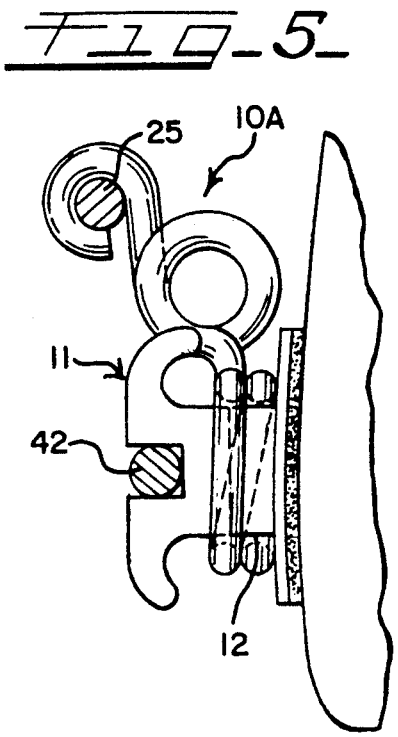
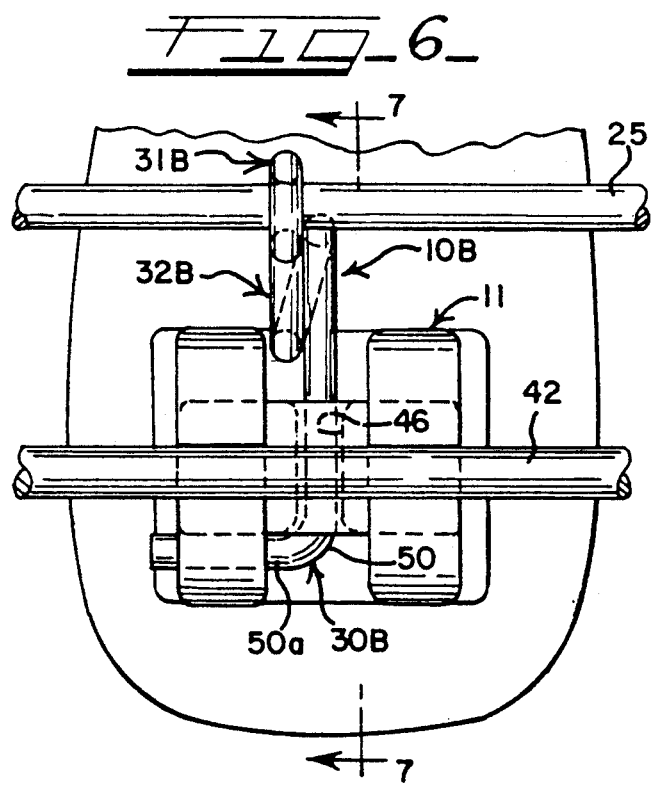
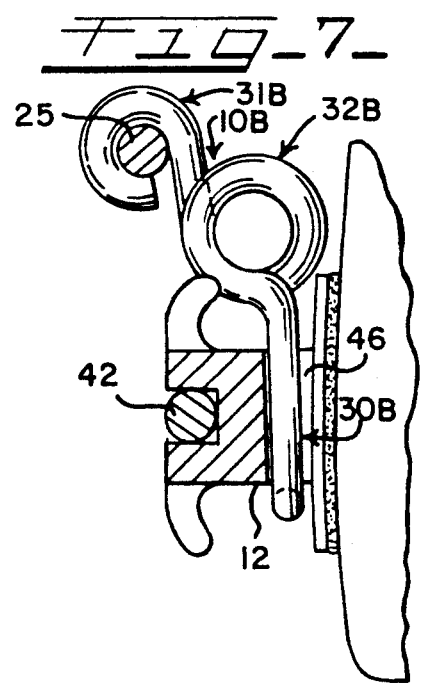

5,035,614

INTRUDING AND TORQUING AUXILIARY

This invention relates in general to an intruding and torquing auxiliary for effecting intruding and/or torquing movements to upper anterior teeth, and more particularly to an auxiliary in the form of a spring connecting member extending between the main archwire or brackets and an auxiliary archwire activated to move generally gingivally.

BACKGROUND OF THE INVENTION

Heretofore, there have been known many appliances for applying torquing forces to teeth as it is common during orthodontic treatment to require torquing forces on teeth and particularly the upper anteriors. Such torquing appliances usually are mounted on the brackets and arranged to either torque the crown or root of a tooth.

An example is shown in U.S. Pat. No. 3,262,207, where an auxiliary archwire is anchored to lock pins of a bracket for applying the torquing forces to the teeth.

Another example of a torquing appliance is shown in U.S. Pat. No. 3,256,602, which in one embodiment, as illustrated in FIG. 13, shows a torquing spring member anchored in the vertical slot of a bracket and then connected to an auxiliary archwire. This appliance serves to retract and/or torque canines and first bicuspids. Its function is not to produce an intrusion force.

However, none of the torquing auxiliaries heretofore known including those disclosed in the above patents are capable of additionally producing an intrusion force for intruding teeth.

SUMMARY OF THE INVENTION

The auxiliary of the present invention obviates the deficiencies of prior known torquing appliances in that it is capable of additionally providing intrusion forces at the same time that it produces torquing forces. The present invention is therefore capable of facilitating orthodontic treatment where intrusion and torquing of a tooth is desired.

In one embodiment, the auxiliary includes a unique structure in that it is provided with a rectangular opening at one end to fit over rectangular archwire so that it can be anchored to the main archwire that is connected to the brackets. The auxiliary extends gingivally and further includes a coil area to define a spring action and terminates in a hook for attachment to an auxiliary archwire activated to produce a generally gingivally directed force.

The auxiliary archwire is slidably held at its terminal ends in buccal tubes. The connection of the appliance to the rectangular wire with adjacent brackets on the upper anterior teeth enables an intruding and torquing force to be applied to the wire for simultaneously effecting intrusion and torquing of the root in a lingual direction. Preferably, the auxiliary is mounted at the midline between the brackets on the upper centrals and would apply a force to whatever brackets the archwire is connected. If it is likewise connected to the laterals as well as the centrals, the intrusion and torquing force would be applied to the laterals as well as the centrals. It may be advisable to utilize two auxiliaries in this situation, each mesial to the left and right central incisor bracket. If the auxiliaries are connected distal to the lateral incisors, the amount of intrusion would increase relative to the amount of torque. The gingival force applied to the hook portion of the auxiliary would activate the coil spring to in turn apply an intruding and torquing movement to the teeth through the archwire.

In another embodiment where it may only be desired to apply a torquing and intrusion force to a single tooth, the auxiliary would have a tail for anchoring in a vertical slot of the bracket. Otherwise, it would include the coil spring portion and the hook portion for connecting to an auxiliary archwire. Use of this embodiment for only applying forces to the tooth on which the bracket is mounted would use a round main archwire in the archwire slot of the bracket as the force would be applied from the auxiliary archwire directly to the bracket and the tooth. However, if the main archwire was rectangular and filled the archwire slot, the intruding and torquing force applied by the auxiliary would likewise be applied to adjacent teeth. In this embodiment, the tail would be bent over the occlusal or incisal end of the bracket to lock the auxiliary in place on the bracket.

In another embodiment, the anchoring portion would include a box frame that would fit over the base of the bracket and a tail that would be received in the vertical slot of the bracket. Because of the box frame lock to the bracket, it would not be necessary to bend the tail over the incisal end of the bracket base. This embodiment would otherwise function just like the embodiment immediately described above.

It is therefore an object of the present invention to provide a new and improved auxiliary for obtaining intruding and torquing forces at the same time on upper anterior teeth.

A further object of the present invention is in the provision of an intruding and torquing auxiliary for connecting between a rectangular archwire or a bracket and an auxiliary archwire for simultaneously applying intruding and torquing forces.

Other objects, features and advantages of the invention will be apparent from the following detailed disclosure, taken in conjunction with the accompanying sheets of drawings, wherein like reference numerals refer to like parts.

DESCRIPTION OF THE DRAWINGS

FIG. 1 is a perspective view of an orthodontic system on the upper arch which includes the intruding and torquing appliance of the invention;

FIG. 2 is a greatly enlarged front elevational view of the anterior centrals having brackets and illustrating one embodiment of the invention where the auxiliary is formed to be connected to a rectangular archwire;

FIG. 3 is a vertical sectional view taken substantially along line 3—3 of FIG. 2 and showing the auxiliary in side elevation;

FIG. 4 is a front elevational view of a modified auxiliary mounted directly on a bracket;

FIG. 5 is a vertical sectional view taken substantially along line 5—5 of FIG. 4 and showing the auxiliary in side elevation;

FIG. 6 is a view like FIG. 4 but illustrating a still further modified auxiliary where the auxiliary is connected to the bracket by a tail inserted in a vertical slot; and FIG. 7 is a vertical sectional view taken substantially along line 7—7 of FIG. 6 and showing the auxiliary in side elevation.

DESCRIPTION OF THE INVENTION

The intruding and torquing auxiliary of the invention is in the form of a spring member, one end of which is connected non-rotatively to a rectangular archwire that is the main archwire or to a bracket, and the other end of which is connected to a secondary or auxiliary archwire disposed gingival to the brackets and gingivally activated. A coil is disposed between the ends of the auxiliary, and as the activated auxiliary archwire attempts to move gingivally, it applies through the auxiliary an intrusive and torquing force to whatever teeth that are interconnected to the auxiliary through the rectangular archwire or through a bracket.

So, wherever both intrusive and torquing forces are needed for anterior teeth in order to correct malposition, the auxiliary of the present invention is useful in order to accomplish the intruding and torquing forces simultaneously so as to expedite treatment.

Referring now to the drawings and particularly to the embodiment of the auxiliary illustrated in FIGS. 1 to 3, the intruding and torquing auxiliary of the invention, generally indicated by the numeral 10, is of the form that will mount in a non-rotative fashion on the main rectangular archwire and be connected to a gingivally disposed round auxiliary archwire. For example, the main wire may be 0.021×0.025 and the round auxiliary wire may be 0.018, although any compatible sizes may be used. The auxiliary is used in this embodiment in connection with standard edgewise brackets mounted on the teeth with a suitable bonding adhesive, although they may be mounted on the teeth in any other suitable manner. Each of the brackets, which are generally designated by the numeral 11, includes a base 12, a pair of parallel spaced tie wings 13 and 14 extending from the base, and an archwire slot in the tie wings defined by the aligned slots 13a and 13b of the tie wings 13 and 14, wherein the slot is horizontally opening and rectangular in cross section. It will be appreciated that other types of archwire brackets that may be pretorqued may be provided and similarly the bracket may only include a single tie wing.

A main rectangular archwire 18 is suitably ligated in the archwire slots of the central and lateral incisor brackets. The archwire shown terminates distal to the laterals. Brackets are shown on the cuspid and bicuspids but would not be normally used in this stage of treatment. A buccal tube 20 including a lower tube 21 and an upper tube 22 that is gingival to the lower tube is provided to receive the auxiliary archwire and optionally other archwires used in other stages of treatment. If the main archwire 18 is carried further distally of the lateral incisors, the intrusive and torquing forces will be progressively dissipated.

In this embodiment, the auxiliary 10 is connected at one end of the main archwire 18 and at the other end which is gingival thereto to an auxiliary or secondary archwire 25 that is slidably anchored in the upper tubes 22 of the buccal tubes 20. As above mentioned, the main archwire 18 is ligated to the brackets by means of elastic or stainless steel ligatures 28. It will be appreciated that other metal ligatures may be used if so desired. While the main archwire is shown to be connected to each of the brackets on the anterior teeth, it will be appreciated that the main archwire may be selectively connected to any number or all of the brackets.

Another embodiment of the invention is shown in FIGS. 4 and 5, wherein the auxiliary is connected directly to a bracket rather than to the archwire and where it might only apply an intruding and torquing force to a single tooth, and where the main archwire may be round. However, if the main archwire is rectangular in order to fill the archwire slots, the auxiliary would then act through the archwire on other adjacent teeth.

Referring to the embodiment of FIGS. 4 and 5, the auxiliary is identified as 10A, having a first end 30A, a second end 31A, and an intermediate coil portion 32A. The first end 30A is formed to be able to surround the base of the bracket and also be anchored in the vertical slot of the bracket. The makeup of the first end is such that it takes the shape of a box frame that can circumvent the base 12 and which includes a tail 45 that extends through the vertical slot 46 of the bracket. The tail 45 is bent over at 45a, although it need not be bent over and may merely be clipped at the occlusal end of the vertical opening 46. The intermediate coil portion 32A extends centrally of the box frame and gingivally up to the first end 31A which is in the form of a hook to hook over the auxiliary archwire 25.

The round archwire 42 in the slot will not impart the forces of the auxiliary toward any of the adjacent brackets, and therefore the auxiliary 10A will only apply an intruding and torquing force on the tooth 46 to which the bracket 11 is mounted. Thus, in the embodiment of FIGS. 4 and 5, the rectangular frame at the first end of the auxiliary serves to lock the auxiliary in place and prevent it from rotating relative to the bracket as the intruding and torquing force applied through the auxiliary and the secondary archwire 25 is applied directly to the bracket and the tooth upon which it is mounted. If a rectangular wire is used in the archwire slot and connected to adjacent brackets, the force applied by the auxiliary will also be applied to adjacent brackets and teeth. As illustrated, with the round wire being the main archwire, the intruding and torquing force is only applied to the tooth on which the bracket is mounted where the auxiliary is connected.

A further embodiment of the invention is shown in FIGS. 6 and 7, which differs from the embodiment of FIGS. 4 and 5 only in that a single tail is provided to anchor the auxiliary in the vertical slot of the bracket. In this embodiment, the auxiliary is identified in general as 10B, having a first end 30B, a second end 31B, and intermediate coil portion 32B. The first end is in the form of a tail 50 which, after being inserted in the vertical slot 46 of the bracket, is bent over the occlusal end of the base at 50A in order to lock the auxiliary to the bracket 11. This auxiliary functions in the same manner as the embodiment of FIGS. 4 and 5 in that it will apply the force directly to the bracket and the tooth.

In view of the foregoing, it will be appreciated that the auxiliary of the invention may take different forms, but in each form it will function to be associated with an auxiliary archwire activated to produce a gingival force and which will then not only apply an intruding force to the tooth or teeth upon which it is to act, but also a torquing force.

It will be understood that modifications and variations may be effected without departing from the scope of the novel concepts of the present invention, but it is understood that this application is to be limited only by the scope of the appended claims.

This invention is hereby claimed as follows:

1. In combination with an edgewise bracket mounted on an anterior tooth and having a horizontally opening rectangular archwire slot and one or more tie wings, a rectangular archwire received in the archwire slot, and a secondary round archwire disposed gingival of the bracket and slidably received in buccal tubes mounted on molar teeth, an intruding and torquing auxiliary comprising a first end and a second end, means for connecting said first end non-rotatively to the bracket, said second end extending gingival to the first end and means for connecting said second end to said secondary archwire, said secondary archwire being activated gingivally, and a coil between the first and second ends, said auxiliary being of a resilient material and extending gingivally from said means for connecting said first end to said means for connecting said second end, whereby the auxiliary develops intrusive and torquing forces on the tooth.

2. The auxiliary of claim 1, wherein the rectangular main archwire is connected to a bracket on at least one other anterior tooth.

3. The auxiliary of claim 1, wherein the second end of the auxiliary includes a hook for connection to the secondary archwire.

4. The auxiliary of claim 3, wherein the first end of the auxiliary includes a box frame adapted to fit over the bracket behind the tie wings.

5. The auxiliary of claim 3, wherein the first end of the auxiliary includes a tail received in a vertical slot of the bracket.

6. In combination with an edgewise bracket mounted on an anterior tooth and having a horizontally opening rectangular archwire slot and one or more tie wings, an archwire received in the archwire slot, and an intrusive archwire disposed gingival of the bracket and slidably received in buccal tubes mounted on molar teeth, an intruding and torquing auxiliary comprising a first end and a second end, means for connecting said first end non-rotatively to the bracket, said second end extending gingival to the first end and means for connecting said second end to said intrusive archwire, said intrusive archwire being activated gingivally, and a coil between the first and second ends, said auxiliary being of a resilient material and extending gingivally from said means for connecting said first end to said means for connecting said second end, whereby the auxiliary develops intrusive and torquing forces on the tooth.

7. The combination of claim 6, wherein the archwire received in said bracket archwire slot is round.

8. The combination of claim 7, wherein the first end of the auxiliary includes a box frame adapted to fit over the bracket behind the tie wings.

9. The combination of claim 7, wherein the first end of the auxiliary includes a tail received in a vertical slot of the bracket.

10. In combination with an edgewise bracket mounted on an anterior tooth and having a horizontally opening rectangular archwire slot and one or more tie winds, a rectangular archwire received in the archwire slot, and a secondary round archwire disposed gingival of the bracket and slidably received in buccal tubes mounted on molar teeth, an intruding and torquing auxiliary comprising a first end and a second end, means for connecting said first end non-rotatively to the bracket, wherein the first end of the auxiliary includes a rectangular opening for fitting on the rectangular archwire, said second end extending gingival to the first end and means for connecting said second end to said secondary archwire, wherein the second end of the auxiliary includes a hook for connection to the secondary archwire, said secondary archwire being activated gingivally, and a coil between the first and second ends, said auxiliary being of a resilient material, whereby the auxiliary develops intrusive and torquing forces on the tooth.

* * * * *

UNITED STATES PATENT AND TRADEMARK OFFICE
CERTIFICATE OF CORRECTION

PATENT NO. : 5,035,614

DATED : July 30, 1991

INVENTOR(S) : Raphael L. Greenfield

It is certified that error appears in the above-identified patent and that said Letters Patent is hereby corrected as shown below:

Title page: under "References Cited U.S. PATENT DOCUMENTS"
add the following patents:

```
--3,256,602  6/1966  Broussard et al.  433/21
--3,262,207  7/1966  Kesling           433/21--
```

Col. 6, line 20, change "winds" to --wings--.

Signed and Sealed this

Thirteenth Day of October, 1992

*Attest:*

DOUGLAS B. COMER

*Attesting Officer*    Acting Commissioner of Patents and Trademarks